United States Patent [19]

Okamoto et al.

[11] Patent Number: 5,368,760

[45] Date of Patent: Nov. 29, 1994

[54] METHOD FOR PRODUCTION OF CYSTAMINE AND ALKYLENE OXIDE ADDUCT THEREOF, ADDITIVE FOR AQUEOUS LUBRICANT, AND AQUEOUS LUBRICANT

[75] Inventors: Jun Okamoto, Yokohama; Yujiro Goto, Kawasaki; Masao Kitano, Kamakura; Seiichi Suzuki, Yokohama, all of Japan

[73] Assignee: Nippon Shokubai Co., Ltd., Osaka, Japan

[21] Appl. No.: 82,619

[22] Filed: Jun. 25, 1993

[30] Foreign Application Priority Data

| Jun. 29, 1992 | [JP] | Japan | 4-170863 |
| Jul. 2, 1992 | [JP] | Japan | 4-175541 |
| Jun. 23, 1993 | [JP] | Japan | 5-12397 |
| Jun. 23, 1993 | [JP] | Japan | 5-152398 |
| Jun. 23, 1993 | [JP] | Japan | 5-152399 |

[51] Int. Cl.$^5$ .......................... C10M 135/00
[52] U.S. Cl. .................. 252/47.5; 252/49.3; 564/487; 564/501
[58] Field of Search ............... 252/47.5, 49.3; 564/475, 477, 487, 501

[56] References Cited

U.S. PATENT DOCUMENTS

| 4,578,345 | 3/1986 | Ohno et al. | 430/393 |
| 4,707,434 | 11/1987 | Koboshi et al. | 430/393 |
| 4,780,403 | 10/1988 | Kishimoto et al. | 430/567 |

FOREIGN PATENT DOCUMENTS

| 53-95630 | 8/1978 | Japan . |
| 58-35168 | 3/1983 | Japan . |
| 60-67456 | 4/1985 | Japan . |
| 570427 | 3/1993 | Japan . |
| 540862 | 12/1976 | U.S.S.R. . |

OTHER PUBLICATIONS

European Search Report EP93305063, Oct. 11, 1993.
Patent Abstract of Japan, vol. 8, No. 225, Oct. 1984.
Biochemical Journal, vol. 267, No. 2, Apr. 1990, 291–296.
Chemical Abstracts, vol. 86, No. 15, Apr. 1977, p. 454.

*Primary Examiner*—John Niebling
*Assistant Examiner*—Edna Wong
*Attorney, Agent, or Firm*—Omri M. Behr; Matthew J. McDonald

[57] ABSTRACT

Cystamine is produced by a method which comprises reacting a 2,2-dialkyl thiazolidine represented by the general formula (1):

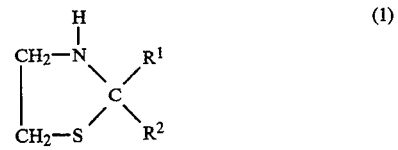

wherein $R^1$ and $R^2$ independently are alkyl groups of 1 to 5 carbon atoms, with a peroxide in the presence of water. An alkylene oxide adduct of cystamine is produced by a method which comprises reacting the reaction mixture obtained as described above further with an alkylene oxide. These cystamine and alkylene oxide adduct of cystamine are useful as an additive for an aqueous lubricant.

15 Claims, No Drawings

METHOD FOR PRODUCTION OF CYSTAMINE AND ALKYLENE OXIDE ADDUCT THEREOF, ADDITIVE FOR AQUEOUS LUBRICANT, AND AQUEOUS LUBRICANT

BACKGROUND OF THE INVENTION

1. Field of the Invention

This invention relates to a method for the production of cystamine and an alkylene oxide adduct of cystamine, an additive for an aqueous lubricant, and an aqueous lubricant containing the additive.

2. Description of the Prior Art

Heretofore, cystamine has been produced by oxidizing cystamine. To be more specific, since cysteamine is unstable in its free state, it is generally procured as a hydrochloride or a sulfate which is stable. This cysteamine salt is oxidized with hydrogen peroxide and purified to a finished product in the form of cystamine hydrochloride or cystamine sulfate. When the cystamine salt is used as a raw material for medicines and agricultural pesticides, for example, the free cystamine moiety of the salt is the necessary principle component and the hydrochloric acid moiety or sulfuric acid moiety of the salt is more often than not discarded as waste. To obtain the free cystamine, the salt must be neutralized with sodium hydroxide and the product of this neutralization separated and purified.

A method for producing cystamine by reacting 2-aminoethyl hydrogensulfide with sodium sulfide in the presence of sulfur (JP-A-58-35,168) and a method for producing cystamine by reacting 2-aminoethyl hydrogensulfide with ammonium polysulfide (JP-A-60-67,456) have been proposed to date. Since these methods require an excess supply of sulfur, they are at a commercialdisadvantage in giving rise to a large amount of inorganic substance as waste, inevitably necessitating complicate operations in the separation of purified cystamine as the end product from the reaction mixture, and requiring a huge amount of time exceeding 30 hours.

As an approach to the production of an alkylene oxide adduct of cystamine, the reaction of a relevant disulfide-containing dihalogen compound with diethanolamine as represented by the following formula has been proposed (USSR Patent No. 540,862).

X—RSSR—X + 2NH(CH$_2$CH$_2$OH)$_2$ ⟶

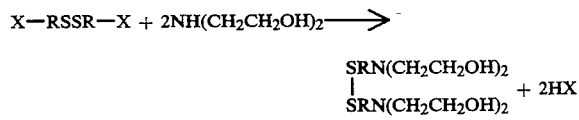

Since this method comprises a deoxidation reaction it requires the supply of diethanol amine in an excess amount of preferably not less than 4 mols. It does not itself constitute a commercially satisfactory solution because the product of the reaction contains an alkylene oxide adduct of cystamine and a large amount of diethanol amine salt and the reaction consequently involves a complicated step for purifying the product. A method for producing a nitrogen-containing disulfide by reacting a nitrogen-containing halogenated hydrocarbon with sodium thiosulfate thereby forming a bunte salt and further heating the reaction product in an acidic state as represented by the following formula has been proposed (JP-A-5-70,427).

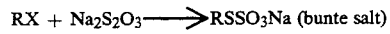

In accordance with this method, since the nitrogen-containing disulfide obtained by the reaction is present in the form of a hydrochloride or a sulfate, it requires a neutralization treatment and the product of this neutralization necessitates an additional complicated purification step because it contains a large amount of an inorganic salt. Since the reaction gives rise to harmful SO$_2$ gas, this harmful gas requires a discarding or recovery step. Thus, this method is not a satisfactory solution from a commercial point of view. Further, a method for producing a nitrogen-containing disulfide by first synthesizing a thiuronium salt from thio-urea and a nitrogen-containing hydrocarbon and then hydrolyzing this thiouronium salt in a basic state has been proposed (JP-A-53-95,630). Since this method produces a large amount of waste as a by product, the step for purifying the reaction product is complicated and the yield is only in the neighborhood of 15%. The reaction of cystamine with an alkylene oxide by dint of the reactivity of amine with epoxy has been well known in the industry concerned. Since the cystamine which is generally obtainable is in the form of cystamine hydrochloride or sulfate, the hydrochloric acid moiety or sulfuric acid moiety of the salt must be refined by neutralization in prior to the reaction.

In recent years, as a consequence of the rapid development of various metal processing techniques, the lubricants used in the processing of metals have been improved in a wide variety of properties.

Heretofore, water-insoluble lubricants have been used for lubricating machines for processing metals. They use mineral oils as a basis and incorporate therein oiliness enhancers (such as animal fats and vegetable oils and surfactants), chlorine type extreme pressure agents (such as chlorinated paraffins and chlorinated oils and fats), and sulfur type extreme pressure agents (such as sulfide oils and fats and sulfide olefins). They have numerous drawbacks such as the imposition of regulations of Fire Prevention Laws because of the composition, adhesion of the lubricant to the metallic surfaces under processing, difficulties encountered separating adhering chips, and defiling the shop interior with lubricant.

For the purpose of eliminating these drawbacks, various water-soluble lubricants have been developed. These lubricants, are at a disadvantage in offering inferior extreme pressure effects, impairing machines and tools in terms of service life and operational accuracy, in ability to control microorganisms, becoming putrid and consequently failing to withstand protracted use. These lubricants eventually exhibit corrosiveness to metals, and induce growth of rust on processed parts and processing devices. At times, the water-soluble lubricants are used mixed with various additives intended to overcome such drawbacks as mentioned above. These mixed lubricants, however, are not fully satisfactory in performance.

This invention, has an object of providing a method for permitting cystamine which is useful as a raw material for medicines and agricultural pesticides to be produced in a free state, by a simple procedure, in high yield, and with ideal qualities advantageous from a commercial point of view.

Another object of this invention is to provide an economically advantageous method for permitting an alkylene oxide adduct of cystamine which is useful for water-soluble lubricants, photographic reagents, antibacterial agents, can cleaning agents, and rust-removing agents to be commercially produced in a free state, in high yield, and by a simple procedure.

Yet another object of this invention is to provide an additive for an aqueous lubricant avoiding the drawbacks of the conventional aqueous lubricant and excelling in quality and also provide an aqueous lubricant.

SUMMARY OF THE INVENTION

The objects described above are accomplished by a method for the production of cystamine, which comprises reacting a 2,2-dialkyl thiazolidine represented by the general formula (1):

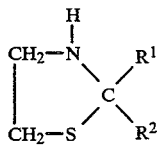
(1)

wherein $R^1$ and $R^2$ independently are an alkyl group of 1 to 5 carbon atoms, with a perioxide in the presence of water.

These objects are further accomplished by a method for the production of an alkylene oxide adduct of cystamine represented by the general formula (2):

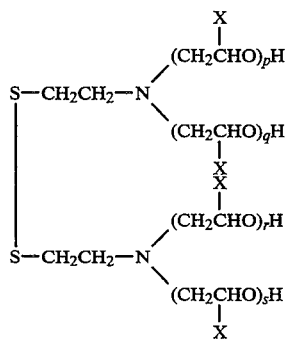
(2)

wherein X is a hydrogen, an alkyl group or phenyl group and p, q, r, and s severally are integers in the range of 0 to 10, providing that the expression of $p+q+r+s \geq 1$, which method comprises reacting a 2,2-dialkyl thiazolidine represented by the general formula (1):

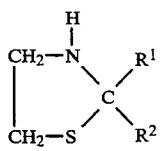
(1)

wherein $R^1$ and $R^2$ independently are an alkyl groups of 1 to 5 carbon atoms, with a peroxide in the presence of water and then reacting an alkylene oxide with the resultant product of the reaction.

These objects are also accomplished by an additive for an aqueous lubricant, which additive comprises a cystamine and/or an alkylene oxide adduct of cystamine represented by the general formula (3).

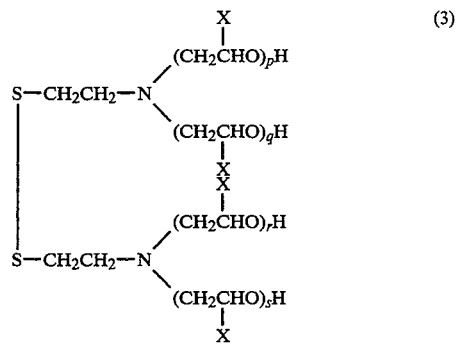
(3)

wherein X is a hydrogen atom or methyl group and p, q, r, and s severally are integers in the range of 0 to 10.

These objects are accomplished by an aqueous lubricant containing 0.1 to 50% by weight of a cystamine and/or an additive comprising an alkylene oxide adduct of cystamine represented by the general formula (3).

By the method of this invention, cystamine which is useful as a raw material for medicines and agricultural pesticides can be obtained in a free state. This method allows commercially advantageous production of cystamine by a simple apparatus and procedure, in high yield, with ideal quality, and with only sparing waste because the reaction proceeds quantitatively and the separation of cystamine from the reaction mixture is easily attained.

The cystamine which is produced by the method of this invention may be further purified suitably by means of distillation and, when necessary, can be easily converted into a derivative such as a hydrochloride.

In accordance with this invention, an alkylene oxide adduct of cystamine which is useful for water-soluble lubricants, photographic reagents, antibacterial agents, can-cleaning agents, and rust-removing agents can be obtained in high yield with sparing waste by a simple procedure which comprises reacting a 2,2-dialkyl thiazolidine with a peroxide in the presence of water and then allowing the resultant reaction product to react with an alkylene oxide.

The additive of this invention for an aqueous lubricant is excellent in extreme pressure effects and has an ability to control microorganisms and, therefore, does not easily become putrid. Further, since it exhibits anticorrosiveness to metals and curbs the growth of rust, it permits production of an aqueous lubricant excellent in such properties as mentioned above.

DESCRIPTION OF THE PREFERRED EMBODIMENT

In accordance with this invention, cystamine represented by the formula (4) and dialkyl ketone represented by the general formula (5):

(4)

(5)

wherein $R^1$ and $R^2$ independently are an alkyl group of 1 to 5 carbon atoms, are produced by reacting a 2,2-dialkyl thiazolidine represented by the general formula (1) with a peroxide in the presence of water.

The 2,2-dialkyl thiazolidines of the general formula (1) for use in this invention, as described above, have the substituents, $R^1$ and $R^2$, which independently are alkyl groups of 1 to 5 carbon atoms, preferably 1 to 3 carbon atoms. As concrete examples of the 2,2-dialkyl thiazolidine which fulfill this requirement, 2,2-dimethylthiazolidine, 2-methyl-2-ethylthiazolidine, 2,2-diethylthiazolidine, 2-methyl-2-propylthiazolidine, 2,2-di-n-propylthiazolidine, 2-methyl-2-n-butylthiazolidine, 2-methyl-2isobutylthiazolidine, 2,2-diisobutylthiazolidine, and 2-methyl-2-pentylthiazolidine may be cited. One member or a mixture of two or more members selected from the group of compounds mentioned above is used.

The peroxides which are usable effectively herein include metal peroxides such as sodium peroxide, magnesium peroxide, zinc peroxide, chromium peroxide, titanium peroxide, and lead peroxide, organic peroxides such as peroxy acids RCOOOH, dialkyl peroxides ROOR, and acyl peroxides RCOOOCOR, hydrogen peroxide, ammonium hydroxide, sulfur peroxide, chlorine peroxide, peroxy-carbonate, nitrogen peroxide, peroxysulfate, and phosphorus peroxide, for example. One member or a mixture of two or more members selected from the group of compounds mentioned above is used. For the purpose of decreasing to the fullest possible extent the waste which occurs during the separation of free cystamine from the reaction mixture after the reaction, it is preferable to use hydrogen peroxide alone.

Hydrogen peroxide is marketed in the form of an aqueous solution. Simply, therefore, the reaction under discussion is effected by adding a commercially available aqueous hydrogen peroxide solution to the 2,2-dialkyl thiazolidine. The reaction may use an inert solvent as for the purpose of enabling this reaction to proceed moderately. The solvents which are usable effectively for this purpose include water, alcohols, ethers, esters, and ketones. One member or a mixture of two or more members selected from the group of solvents mentioned above may be used. From the viewpoint of an economic effect, it is preferable to use water as a reaction solvent herein. Thus, the reaction under discussion may be effected by first preparing an aqueous solution of the 2,2-dialkyl thiazolidine and then adding hydrogen peroxide to the aqueous solution.

Since the reaction proceeds quantitatively, it may suffice for this reaction to use 0.5 mol of a peroxide per 1 mol of a 2,2-dialkyl thiazolidine. Generally, the reaction is carried out by using the peroxide in an amount in the range of 0.4 to 1.0 mol, preferably 0.5 to 0.7 mol, per mol of 2,2-dialkyl thiazolidine. If the peroxide is used in an unduly small amount, unaltered 2,2-dialkyl thiazolidine persist in the reaction mixture. Conversely, if the peroxide is used in an unduly excess amount, the reaction produces cystamine in low yield.

This reaction proceeds exothermically relatively quickly. The reaction is carried out generally at a temperature in the range of $-10°$ to $+100°$ C. Since the yield of cystamine decreases proportionately as the reaction temperature increases, the reaction is preferably carried out at a temperature in the range of $-10°$ to $+30°$ C., most preferably $0°$ C. to $20°$ C. The reaction can be effected under normal pressure, under an increased pressure, or under a decreased pressure.

The reaction mixture obtained at the end of the reaction, when necessary, may be further treated for separation of cystamine in a purified state from the reaction mixture. When hydrogen peroxide is used as the peroxide to take part in the reaction, the by-produced dialkyl ketone and water are expelled from the reaction system by a conventional distillation operation. This distillation produces free cystamine as a residue. By further distilling this residue, cystamine of still higher purity can be obtained. The yield of cystamine is lowered when the temperature used for this additional distillation is unduly high. Thus, this additional distillation is preferably performed under a vacuum at a temperature of not higher than $100°$ C.

The 2,2-dialkyl thiazolidine of the general formula (1) for use in this invention can be synthesized from ethylene imine, hydrogen sulfide and a dialkyl ketone of the general formula (5) (Ann. der Chemie, 566, 210 (1950)).

After the method of the present invention has been carried out, therefore, the dialkyl ketone of the general formula (5) which is discharged from the system during the separation of cystamine is preferably recovered and utilized again as a raw material for the synthesis of 2,2-dialkyl thiazolidine. This measure allows a reduction in the waste and makes the method of production vastly superior from a commercial point of view.

The method for production of an alkylene oxide adduct of cystamine according with this invention comprises first causing a 2,2-dialkyl thiazolidine represented by the general formula (1) to react with a peroxide in the presence of water and then allowing an alkylene oxide to react with the resultant reaction product thereby obtaining an alkylene oxide adduct of cystamine represented by the general formula (2). The reaction which are involved in this procedure may be represented by the following formulas:

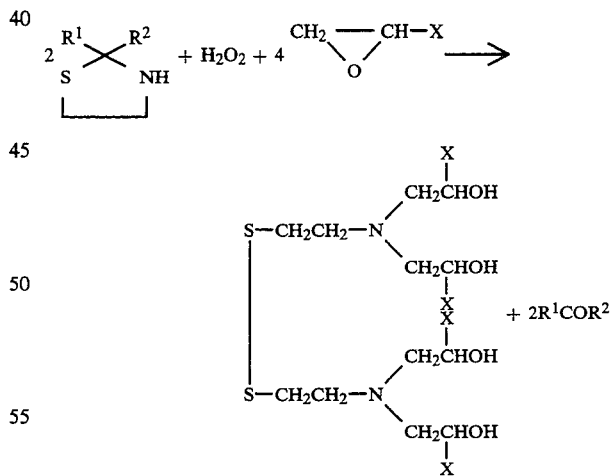

Preferable examples of the alkylene oxide used in this invention are ethylene oxide and propylene oxide. Such alkylene oxides as butylene oxide and styrene oxide are similarly usable. These alkylene oxide may be used solely or as a mixture of at least two kinds.

After the reaction of the 2,2-dialkyl thiazolidine with a peroxide, the subsequent reaction of the resultant reaction solution with the alkylene oxide is generally carried out at a temperature in the range of $20°$ to $200°$ C., preferably $40°$ to $120°$ C. Then, the amount of the alkylene oxide used in the second reaction may be selected in range of the of 1 to 20 mols per mol of the 2,2-dialkyl thiazolidine, depending on the subsequent use of the alkylene oxide adduct of cystamine to be produced. The reaction of the reaction solution mentioned above with the alkylene oxide may be carried out under normal pressure or under an increased pressure. This reaction pressure can be suitably selected, depending on the boiling point of the alkylene oxide and the reaction temperature. After the second reaction has been completed, the alkylene oxide adduct of cystamine, as occasion demands, may be separated in a purified state by distillation or extraction from the reaction mixture comprising the alkylene oxide adduct of cystamine, by-produced dialkyl ketone, and water. Further, when hydrogen peroxide is used as the peroxide, an alkylene oxide adduct of cystamine of high purity can easily be obtained by removing the by-produced dialkyl ketone, water and a reaction solvent under normal pressure or under a reduced pressure. The dialkyl ketone which is consequently recovered can be utilized as a raw material for the synthesis of 2,2-dialkyl thiazolidine.

The compound of the general formula (3) according to this invention produces excellent extreme pressure effects because it structurally contains organic sulfur atoms, shows an ability to proof metals against corrosion because it contains amino groups, and exhibits wettability because it contains a poly-alcohol. It further is endowed with high water-solubility and an ability to control microorganisms. This compound, therefore, itself constitutes an outstanding additive for an aqueous lubricant.

The additive for the aqueous lubricant according to this invention is a compound represented by the general formula (3)- Typical examples of the compound satisfying the general formula (3) on the condition of $p=q=r=s=0$ include cystamine and on the condition of $p=q=r=s=1$ include N,N,N',N'-tetra(2-hydroxyethyl) cystamine and N,N,N',N'-tetra(2-hydroxypropyl) cystamine. In addition to these typical examples, other compounds which have a mixture of a 2-hydroxyethyl group and a 2-hydroxypropyl group contained in one molecular unit may be cited. The compounds of the general formula (3) satisfying the condition of p, q, r and s being 2 are similarly usable, and p, q, r and s may be different each other. Preferably, p, q, r, and s are independently integers in the range of 1 to 5 and $p+q+r+s$ is 4 to 12.

The aqueous lubricant contemplated by this invention is an aqueous lubricant which contains a compound represented by the general formula (3). Generally, the aqueous lubricant is formed by diluting at least one of the compounds mentioned above in water at a concentration in the range of 0.1 to 50% by weight, preferably 0.5 to 20% by weight. This aqueous lubricant is put to use generally after incorporating therein various additives which are popularly used for aqueous lubricant such as those capable of opposing abrasion, preventing corrosion, preventing putrefaction, opposing fungal growth, and precluding formation of foam. The lubricant can be made to acquire an enhanced lubricating capacity by further incorporating therein 1 to 20% by weight of a polyglycol such as polyethylene glycol or polypropylene glycol or a copolymer thereof. The polyglycol or copolymer thereof preferably has an average molecular weight in the range of 200 to 20,000, more preferably 400 to 4,000.

Now, this invention will be described more specifically below with reference to the working examples.

Example 1

In a flask provided with a stirring device, a thermometer, and a dropping funnel, were placed 1,170 g (10 mols) of 2,2-dimethyl thiazolidine and 500 g of water. While they were then kept stirred at a temperature in the range of 5° to 10° C., 544 g (5.6 mols) of an aqueous 35 wt % hydrogen peroxide solution was added dropwise over a period of about two hours, and the resultant mixture was left reacting at 10° C. for 1 hour following the completion of the dropwise addition. When a sample of the resultant reaction solution was assayed by liquid chromatography, it was found that this solution contained cystamine at a concentration of 34% by weight, a value which indicates that the reaction yield was 99%. Then, the reaction solution was heated to 100° C. under a vacuum to expel by-produced acetone and water by distillation and obtain cystamine as a residue. When the residue was subjected to quantitative assay by liquid chromatography, the yield of the cystamine was found to be 94%.

The cystamine thus obtained was further purified by vacuum distillation with a thin-film still kept at a pressure of 1 mmHg and a temperature of 145° C. On assay by liquid chromatography, the purified cystamine was found to have a purity of 99.0%.

EXAMPLE 2

The procedure of Example 1 was repeated, except that 1,170 g(10 mols) of 2,2-dimethyl thiazolidine, 160 g of water, and 777 g (8 mols) of an aqueous 35 wt % hydrogen peroxide solution were used instead.

When the cystamine obtained after removal by distillation of the by-produced acetone and water was subjected to quantitative analysis by liquid chromatography, the yield thereof was found to be 84%.

EXAMPLE 3

In a pressure reaction vessel made of stainless steel and provided with a stirring device and a thermometer, 1,170 g (10 mols) of 2,2-dimethyl thiazolidine and 500 g of water were placed and, while they were kept stirred at a temperature in the range of 5° to 10° C., 544 (0.56 mol) of an aqueous 35 wt % hydrogen peroxide solution was added dropwise thereto over a period of about 2 hours, the resultant mixture were left standing at 10° C. for 1 hour, the mixture was kept at an elevated temperature of 50° C. and 880 g (20 mols) of ethylene oxide was added thereto over a period of about 3.5 hours, and the resultant mixture was left standing at 50° C. for 1 hour following the completion of the addition of the ethylene oxide. The reaction solution obtained consequently was cooled and assayed by liquid chromatography to find that this solution contained the compound shown below in a concentration of 52.5% by weight, a value which indicates that the reaction yield was 99%. When this reaction solution was heated at about 70° C. under a vacuum to expel the by-produced acetone and water by distillation, 2,030 g of a compound of the following formula (6) (aqueous 80 wt % solution) was obtained.

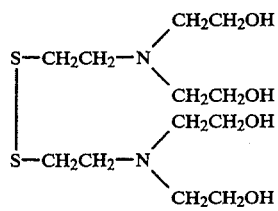

(6)

EXAMPLE 4

When the procedure of Example 3 was repeated, except that 1,760 g (40 mols) of ethylene oxide was used instead, 3,120 g of a compound represented by the below-mentioned formula (7) (aqueous 80 wt % solution) was obtained.

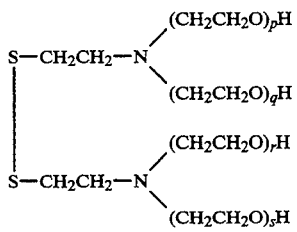

(7)

wherein an average value of p, q, r and s is 2.

EXAMPLE 5

When the procedure of Example 3 was repeated, except that 1,160 g (20 mols of propylene oxide was used instead of ethylene oxide, 2,376 g of a compound represented by the following formula (8) (aqueous 80 wt % solution) was obtained.

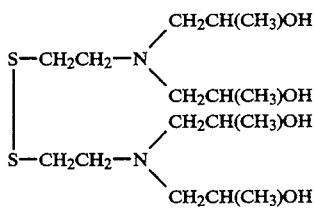

(8)

EXAMPLE 6

When the procedure of Example 3 was repeated, except that 2,320 g (40 mols) of propylene oxide was used instead of ethylene oxide, 3,812 g of a compound represented by the following formula (9) (aqueous 80 wt % solution) was obtained.

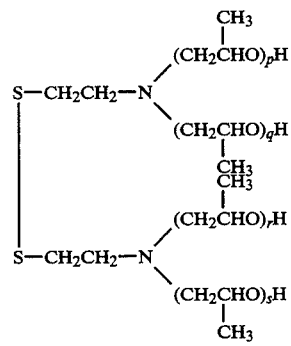

(9)

wherein an average value of p, q, r and s is 2.

In the following examples, the aqueous lubricants obtained therein were tested for the following properties as follows.

Extreme pressure effect

The extreme pressure effect was evaluated in terms of the ability to withstand load. The ability to withstand load was measured in accordance with the Soda's Four-ball Method specified in JIS (Japanese Industrial Standard) K 2519 5 using a Soda's four-ball friction tester. To be specific, with 3 of 4 testing steel balls were fixed to a sample container and the remaining steel ball fixed to a vertical shaft, a sample placed to fill the sample container to capacity, and the vertical shaft kept still, the steel balls were rotated at 200 rpm for 1 minute and kept under a hydraulic pressure of 1.0 kgf/cm$^2$ to find whether or not the steel balls sustained seizure because of the rotation. This procedure was repeated with the testing steel balls and the sample wholly renewed before the start of each repetition and the magnitude of the hydraulic pressure gradually increased with an increment of 0.5 kgf/cm$^2$ to find the acceptable limit load, i.e. the maximum hydraulic load under which the steel balls sustained no seizure. The limit load was reported as the ability of the sample to withstand load.

Quality of lubricity

The quality of lubricity of a sample was evaluated in terms of friction coefficient. The friction coefficient was measured with a Soda's pendulum type oil quality tester and determined on the basis of the damping factor obtained by the measurement just mentioned.

Effect of controlling microorganisms

This property was evaluated by a method for determining the minimum growth inhibiting concentration (MIC) with respect to the following microbes.
1. *Staphylococcus aureus*
2. *Bacillus cereus*
3. *Escherichia coli.*
4. *Pseudomonas aeruginosa*

Liquids were prepared by suspending in physiological saline solution the microbes which had undergone 2 or 3 days of successive transfer culture. The suspensions were severally spread on microbial cultures to which a given lubricant diluted with water had been injected in advance. The microbes thus inoculated were cultured in an incubator at 30° C. for 18 to 20 hours and, at the end of the culture, were tested for growth. The microbial growth was evaluated so as to find the minimum concentration of the lubricant required for perfect inhibition of microbial growth. This minimum concentration was reported as the MIC value.

Anticorrosive effect

Steel plate was dipped into a sample solution and then corrosion state of the steel plate was observed. That is, the steel plate which was previously degreased and polished having 75mm of length, 10mm of width and 1 mm of thickness was changed to a test tube, and the sample solution was poured until half portion of the steel plate was dipped, then open portion of the tube was closed by a cork stopper slightly. Then the test tube was inclined and the steel plate was completely dipped in the sample solution. The test tube was stood vertically for 48 hours, and then the steel plate was removed from the test tube and degree of change of color was observed.

EXAMPLE 7

Cystamine was diluted with tap water to prepare aqueous solutions containing cystamine at 3 concentrations, 0.6% by weight, 1.2% by weight, and 2.4% by weight, and were labeled sequentially as Sample No. 1, No. 2, and No. 3. These samples were tested for the properties of an aqueous lubricant. For control, this test was conducted on a comparative sample formed solely of tap water.

The results for the test of the ability to withstand load and the friction coefficient are shown in Table 1.

TABLE 1

| Sample No. | S content in sample (%) | ability to withstand load (kgf/cm$^2$) | friction coefficient |
|---|---|---|---|
| 1 | 0.2 | 2.0 | 0.13 |
| 2 | 0.5 | 3.0 | 0.12 |
| 3 | 1.0 | 4.0 | 0.12 |
| tap water | 0 | 0.5 | 0.20 |

EXAMPLE 8

N,N,N',N'-tetra(2-hydroxyethyl) cystamine was diluted with tap water to prepare aqueous solutions containing the compound at 3 concentrations, 1.0% by weight, 2.5% by weight, and 5.0% by weight, and were labeled sequentially as Sample No. 4, No. 5, and No. 6. These samples were tested for the properties of an aqueous lubricant.

The results for the test of the ability to withstand load and the friction coefficient are shown in Table 2.

TABLE 2

| Sample No. | S content in sample (%) | ability to withstand load (kgf/cm$^2$) | friction coefficient |
|---|---|---|---|
| 4 | 0.2 | 2.0 | 0.13 |
| 5 | 0.5 | 3.5 | 0.12 |
| 6 | 1.0 | 4.5 | 0.11 |

EXAMPLE 9

N,N,N',N'-tetra(2-hydroxypropyl) cystamine was diluted with tap water to prepare aqueous solutions containing the compound at 3 concentrations, 1.2% by weight, 3.0% by weight, and 6.0% by weight, and were labeled sequentially as Sample No. 7, No. 8, and No. 9. These samples were tested for the properties of an aqueous lubricant.

The results for the test of the ability to withstand load and the friction coefficient are shown in Table 3.

TABLE 3

| Sample No. | S content in sample (%) | ability to withstand load (kgf/cm$^2$) | friction coefficient |
|---|---|---|---|
| 7 | 0.2 | 2.5 | 0.12 |
| 8 | 0.5 | 4.0 | 0.12 |
| 9 | 1.0 | 5.0 | 0.11 |

EXAMPLE 10

An ethylene oxide adduct of cystamine represented by the following formula (10) was diluted with tap water to prepare aqueous solutions containing the compound at 3 concentrations, 2.1% by weight, 5.3% by weight, and 10.6% by weight, and were labeled sequentially as Sample No. 10, No. 11, and No. 12. These samples were tested for the properties of an aqueous lubricant.

The results for the test of the ability to withstand load and the friction coefficient are shown in Table 4.

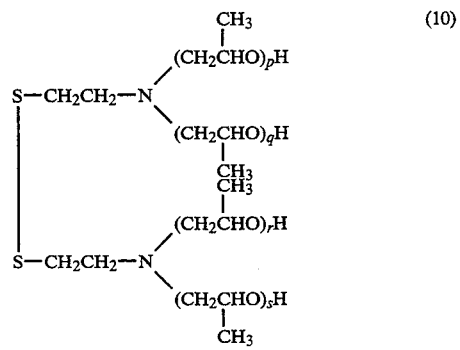

(10)

wherein an average value of p, q, r and s is 2.

TABLE 4

| Sample No. | S content in sample (%) | ability to withstand load (kgf/cm$^2$) | friction coefficient |
|---|---|---|---|
| 10 | 0.2 | 2.0 | 0.12 |
| 11 | 0.5 | 3.0 | 0.12 |
| 12 | 1.0 | 4.5 | 0.11 |

EXAMPLE 11

An aqueous solution containing 3.0% by weight of N,N,N',N'-tetra(2-hydroxypropyl) cystamine and 10% by weight of polyethylene glycol having an average molecular weight of 3,000 was diluted with tap water to obtain Sample No. 13. This sample was tested for the properties of an aqueous lubricant.

The results for the test of the ability to withstand load and the friction coefficient are shown in Table 5.

TABLE 5

| Sample No. | S content in sample (%) | ability to withstand load (kgf/cm$^2$) | friction coefficient |
|---|---|---|---|
| 13 | 0.5 | 4.5 | 0.10 |

EXAMPLE 12

N,N,N',N'-tetra(2-hydroxypropyl) cystamine was tested for its ability to control microbes. The results of the test are shown in Table 6. From the results, it is clearly noted that this compound was effective in controlling microbes at an ordinary application rate in the range of 0.5 to 20% by weight.

TABLE 6

| Microorganism | MIC value |
|---|---|
| *Staphylococcus aures* | 0.5% |
| *Bacillus cereus* | 0.3% |
| *Escherichia coli* | 0.4% |
| *Pseudomonas aeruginosa* | 1.0% |

EXAMPLE 13

N,N,N',N'-tetra(2-hydroxyproyl) cystamine was diluted with tap water to prepare aquous solutions containing the compound at 3 concentrations, 0.5% by weight, 5.0% by weight, and 20% by weight, and anticorrosive effect to a steel plate of each aqueous solution was observed. At the same time, corrosive degree of water used for dilution to the steel plate was also observed for control.

The results for the test of anticorrosive effect are shown in Table 7. It is clear that the compound having 0.5 to 20% by weight of the concentration has anticorrosive effect.

TABLE 7

| Concentration of samples (% by weight) | State of steel plate after test |
| --- | --- |
| 0 | Rust generated on whole surface |
| 0.5 | No Change |
| 5.0 | No Change |
| 20 | No Change |

What is claimed is:

1. A method for the production of cystamine, which comprises reacting a 2,2-dialkyl thiazolidine represented by the general formula (1):

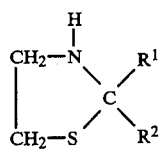
(1)

wherein $R^1$ and $R^2$ independently are alkyl groups of 1 to 5 carbon atoms, with a peroxide in the presence of water.

2. A method according to claim 1, wherein said peroxide is hydrogen peroxide.

3. A method according to claim 1, wherein $R^1$ and $R^2$ in said general formula (1) independently are alkyl groups of 1 to 3 carbon atoms.

4. A method according to claim 1, wherein the amount of said peroxide is in the range of 0.4 to 1.0 mol, based on 1 mol of said 2,2-dialkyl thiazolidine.

5. A method according to claim 1, wherein said reaction is carried out at a temperature in the range of $-10°$ to $+100°$ C.

6. A method for the production of an alkylene oxide adduct of cystamine represented by the general formula (2):

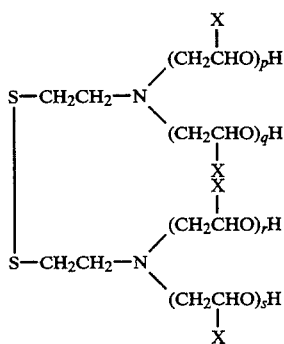
(2)

wherein X is a hydrogen atom, an alkyl group or phenyl group and p, q, r, and s independently are integers in the range of 0 to 10, providing the expression, $p+q+r+s \geq 1$, is fulfilled, which comprises reacting a 2,2-dialkyl thiazolidine represented by the general formula (1):

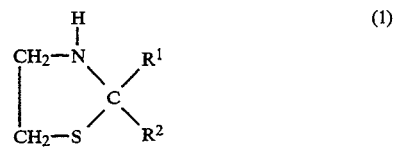
(1)

wherein $R^1$ and $R^2$ independently are alkyl groups of 1 to 5 carbon atoms, with a peroxide in the presence of water and then reacting an alkylene oxide with the resultant product of the reaction.

7. A method according to claim 6, wherein said peroxide is hydrogen peroxide.

8. A method according to claim 6, wherein said alkylene oxide is selected from the group consisting of ethylene oxide and propylene oxide.

9. A method according to claim 6, wherein $R^1$ and $R^2$ in said general formula (1) independently are alkyl groups of 1 to 3 carbon atoms.

10. A method according to claim 6, wherein the amount of said alkylene oxide used is in the range of 1 to 20 mols, based on 1 mol of said 2,2-dialkyl thiazolidine.

11. An additive for an aqueous lubricant represented by the general formula (3):

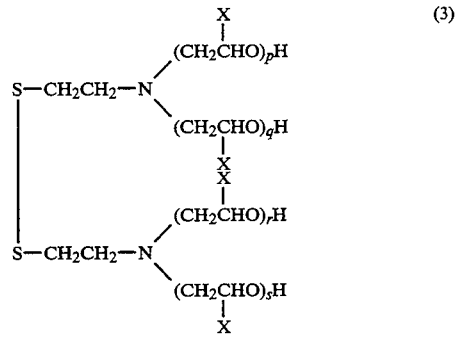
(3)

wherein X is a hydrogen atom or a methyl group and p, q, r, and s independently are integers in the range of 0 to 10.

12. An additive according to claim 11, wherein p, q, r, and s in said general formula (3) independently are integers in the range of 1 to 5 and $p+q+r+s$ is 4 to 12.

13. An aqueous lubricant containing 0.1 to 50% by weight of an additive comprising a cystamine and/or an alkylene oxide adduct of cystamine represented by the general formula (3):

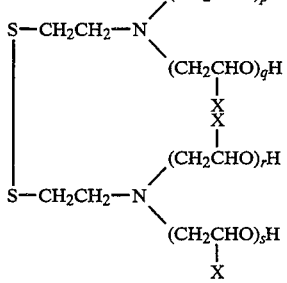
(3)
wherein X is a hydrogen atom or a methyl group and p, q, r, and s independently are integers in the range of 0 to 10.
14. An aqueous lubricant according to claim 13, wherein p, q, r, and s in said general formula (3) independently are integers in the range of 1 to 5 and $p+q+r+s$ is 4 to 12.
15. An aqueous lubricant according to claim 13, which contains 1 to 20% by weight of a polyglycol or a copolymer thereof.
* * * * *